(12) United States Patent
Doemling et al.

(10) Patent No.: US 6,699,883 B1
(45) Date of Patent: Mar. 2, 2004

(54) PYRROLOIMIDAZOLE DERIVATIVES AND THEIR USE AS MEDICAMENTS

(75) Inventors: Alexander Doemling, München (DE); Barbara Beck, München (DE)

(73) Assignee: Morphochem AG, München (DE)

( * ) Notice: Subject to any disclaimer, the term of this patent is extended or adjusted under 35 U.S.C. 154(b) by 0 days.

(21) Appl. No.: 10/089,917

(22) PCT Filed: Oct. 9, 1999

(86) PCT No.: PCT/EP00/09904

§ 371 (c)(1),
(2), (4) Date: Apr. 4, 2002

(87) PCT Pub. No.: WO01/25213

PCT Pub. Date: Apr. 12, 2001

(30) Foreign Application Priority Data

Oct. 7, 1999 (DE) .......................... 199 48 417

(51) Int. Cl.[7] ...................... A61K 31/445; A61K 31/40; C07D 401/14; C07D 403/04
(52) U.S. Cl. ...................... 514/323; 514/397; 546/201; 548/312.1
(58) Field of Search ...................... 548/312.1; 514/397, 514/323; 546/201

(56) References Cited

PUBLICATIONS

Suvorov et al, Khim.Farm. Zh. (1970) vol. 4(2), p. 10–12; Chem. Abstracts (1970) vol. 72, Abstract No. 132619e.*
Elisabete Rodrigues Pereira et al., *Syntheis and Biological Evaluation of Monoindolyl and Indolocarbazolyl Oxazolones and Imidazolones*, Chem. Pharm. Bull. 45(4) 733–736 (1997).
Ikuo Kawasaki et al., *Total Synthesis of Nortopsentins A–D, Marine Alkaloids*, Chem. Pharm. Bull. 44(10) 1831–1839 (1996).
Ines Mancini et al., *From Inactive Nortospentin D. a Novel Bis(indole) Alkaloid Isolated from the Axinellid Sponge Dragmacidon sp. From Deep Waters South of New Caledonia. to a Strongly Cytotoxic Derivative*, Helvetica Chimica Acta Vol 79 (1996) 2075–2082.
Said Achab et al., *An Expeditious Synthesis of Structural Analogs of the Marine Cytotoxic Agents Grossularines–1 and –2*. Tetrahedron Letters, vol. 36, No. 15, pp. 2615–2618 (1995).
Donald P. Matthews et al., *Synthesis and Cardiotonic Activity of Novel Biimidazoles*, J. Med. Chem. 1990, 33, 317–327.
Shinji Tsujii et al., *Topsetin, Bromotopsetin, and Dihydrodeoxybromotopsentin: Antiviral and Antitumor Bis(indolyl)imidazoles from Caribbean Deep–Sea Sponges of the Family Halichondriidae. Structural and Synthetic Studies*, J. Org. Chem. 1988, 53, 5446–5453.
Tommaso Ajello et al, *Heterocyclic glyoxylic aldehydes*. Chemical Abstr. vol. 51, 17935–17936.
Kawasaki et al., *Synthesis of O–methyltopsentin*. Chemical Abstr. vol. 125, No. 15, p. 1257, (1996) No. 196085y.
Kawasaki et al., *Total synthesis of topsentin, antiviral and antitumor bis(indolyl)imidazole*. Heterocycle. 1998, 48, 1887–1901 Chemical Abstr. 1999, vol. 130, No. 25218t.

* cited by examiner

*Primary Examiner*—Bernard Dentz
(74) *Attorney, Agent, or Firm*—Peter F. Corless; John B. Alexander; Edwards & Angell, LLP

(57) ABSTRACT

The present invention relates to 3-pyrroloimidazole derivatives of the general formula (I)

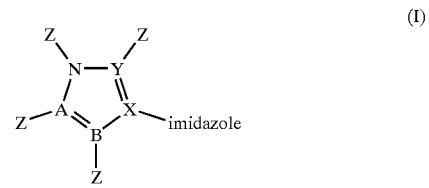

wherein the imidazole radical is an optionally substituted imidazole ring, X, Y, A and B are, each independently of the others, carbon or nitrogen atoms, the radicals Z denote, each independently of the others, a hydrogen atom, a halogen atom, a pseudohalogen, an optionally substituted alkyl, alkenyl, alkynyl, aralkyl, aralkenyl, aralkynyl, cycloalkyl, cycloalkenyl, cycloalkynyl, cycloaralkyl, cycloaralkenyl, cycloaralkynyl, aryl or alkoxy radical or an optionally substituted ring, to which one or two further, optionally substituted rings may be fused, and/or at least two of the radicals Z may be part of an optionally substituted ring, to which one or two further, optionally substituted rings may be fused, and to pharmaceutical compositions comprising at least one of the above-mentioned compounds, optionally in combination with carriers and/or adjuvants and/or excipients customary per se.

17 Claims, No Drawings

PYRROLOIMIDAZOLE DERIVATIVES AND THEIR USE AS MEDICAMENTS

This application is a 371 of PCT/EP00/09904 filed Oct. 9, 1999.

The present invention relates to new 3-pyrroloimidazole derivatives, to pharmaceutical compositions comprising them, to the preparation and use thereof, especially as tumour- and cancer-lysing and more especially as antibiotic, very especially antibacterial, medicaments.

Cancer and tumour diseases are among civilisation's problematic clinical entities. In many cases, the tumour tissue has to be surgically removed and/or treated by chemotherapy. Long-term patient survival is, however, very uncertain. Moreover, chemotherapy and surgical treatment frequently involve pain and other problems for the cancer patient. The provision of new, complementary medicaments for the treatment of tumour and cancer diseases is, therefore, of great interest. Also, it can be assumed, in the light of the general increase in the formation of resistance in micro-organisms and bacteria, that there exists a need for new and similarly active, or even more active, antibiotics.

The problem of the present invention was accordingly to provide new active ingredients having improved and/or complementary action in the prophylaxis and/or therapy of cancer and tumours and/or especially strong antibiotic, more especially antibacterial, activity in the prophylaxis and/or combating/therapy of infections by micro-organisms.

The problems are solved by provision of 3-pyrroloimidazole derivatives of the general formula (I):

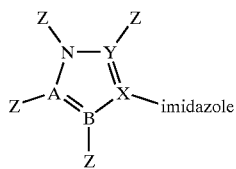

wherein
the imidazole radical is an optionally substituted imidazole ring, which may also be present in salt form, X, Y, A and B are, each independently of the others, carbon or nitrogen atoms, X, Y, A and B preferably being carbon atoms, the radicals Z can denote, each independently of the others, a hydrogen atom, a halogen atom, a pseudohalogen, an optionally substituted alkyl, alkenyl, alkynyl, aralkyl, aralkenyl, aralkynyl, cycloalkyl, cycloalkenyl, cycloalkynyl, cycloaralkyl, cycloaralkenyl, cycloaralkynyl, aryl or alkoxy radical and/or an optionally substituted ring, to which one or two further, optionally substituted rings may be fused, and/or at least two of the radicals Z may be part of an optionally substituted ring, to which one or two further, optionally substituted rings may be fused. The radicals Z preferably are, each independently of the others, a hydrogen atom, a halogen atom or a pseudohalogen, more preferably a hydrogen atom, fluorine, chlorine, bromine or iodine, most preferably a hydrogen atom.

Preferably, the radicals Z—A=B—Z together have the formula

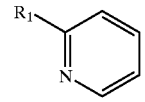

wherein $R_1$ is a substituent, preferably a group of formula —G— substituted $C_1$–$C_6$alkyl, such as —G—$C_1$–$C_6$alkyl-aryl, especially —G-benzyl; —G-aryl; —G—$C_1$–$C_6$alkyl; —G-cycloalkyl; —G-heterocycloalkyl; —G—$C_1$–$C_6$alkyl-heteroaryl, wherein G is $CH_2$, O, N or S, preferably O, or $R_1$ is an aryl, heteroaryl, cycloalkyl, heterocycloalkyl or cycloalkenyl, and wherein the radicals Z bonded to N and Y are, each independently of the other, $C_1$–$C_6$alkyl radicals, such as methyl radicals, cycloalkyl radicals or H atoms, preferably H atoms.

Throughout the description and the claims, the expression "alkyl" can denote, for example, a $C_{1-50}$alkyl group, preferably a $C_{1-12}$alkyl, especially a $C_{1-6}$alkyl group; for example, an alkyl group may be a methyl, ethyl, propyl, isopropyl or butyl group;

the expression "alk", for example in the expression "alkoxy", is defined as for "alkyl";

"aromatic compounds" or "aryls" or corresponding radicals are, for example, substituted or optionally unsubstituted phenyl, benzyl, naphthyl, biphenyl or anthracene groups or aromatic heterocycles having 5 or 6 ring atoms;

the expression "ar", for example in the expressions "aralkyl", "aralkenyl", "aralkynyl"etc. and "cycloaralkyl", "cycloaralkenyl", "cycloaralkynyl" etc., is defined as for "aryl";

the expression "alkenyl" can denote, for example, a $C_{2-10}$alkenyl group, preferably a $C_{2-6}$alkenyl group, which has the double bond(s) at any desired location and may be unsubstituted or substituted; for example, an ethenyl, propenyl, isopropenyl or butenyl group;

the expression "alkynyl" can denote, for example, a $C_{2-10}$alkynyl group, preferably a $C_{2-6}$alkynyl group, which has the triple bond(s) at any desired location and may be unsubstituted or substituted; for example, an ethynyl, propynyl, isopropynyl or butynyl group;

the expression "cycloalkyl" can denote, for example, an optionally substituted carbocycle having from 3 to 20 C atoms, preferably having from 5 to 15 C atoms and especially having 5 or 6 C atoms, which has no multiple bond in the carbocycle;

the expression "cycloalkenyl" can denote, for example, an optionally substituted carbocycle having from 3 to 20 C atoms, preferably having from 5 to 15 C atoms and especially having 5 or 6 C atoms, which has at least one double bond in the carbocycle;

the expression "cycloalkynyl" can denote, for example, an optionally substituted carbocycle having from 3 to 20 C atoms, preferably having from 5 to 15 C atoms and especially having 9 or 10 C atoms, which has at least one triple bond in the carbocycle;

the expression "alkoxy" can denote, for example, a group of formula —O-alkyl, —O-alkenyl, —O-alkynyl, —O-cycloalkyl, —O-cycloalkenyl, —O-cycloalkynyl or —O-aryl, the expression "heteroaroyl" can denote, for example, 5-6-membered heterocyclic aromatic heterocycles having 1, 2 or 3 hetero atoms, for example substituted (as defined hereinbelow) pyrrole, furan, thiophene pyrazole, isoxazole, isothiazole, imidazole, oxazole, thiazole 1,2,4-triazole, 1,2,4-oxadiazole, 1,2,4- thiadiazole, 1,2,5-oxadiazole, 1,2,5-thiadiazole, tetrazole, pyridine, pyrylium, thiapyrylium, pyridazine, pyrimidine, pyrazine, 1,2,3-triazine, 1,2,4-triazine, 1,3,5-triazine, 1,2,3,4-tetrazine, 1,2,3,5-tetrazine, 1,2,4,5-tetrazine, indole, coumarone, thio-naphthene, carbazole, bibenzofuran, dibenzothiophene, 1H-indazole, indoxazole, benzo[d]isothiazole, anthranile, benzimidazole, benzoxazole, benzothiazole, benzotriazole, quinoline, isoquinoline, benzopyrylium, thiabenzopyrylium, acridine, benzo[g]quinoline, benzo[g]isoquinoline, benzo[c]quinoline, cinnoline, phthalazine, quinazoline, quinoxaline, phenazine, benzo[g]cinnoline, benzo[g]quin-azoline, benzo[g] quinoxaline, 1,5-naphthyridine, 1,6-naphthyridine, 1,7-naphthyridine, 1,8-naphthyridine, 2,6-naphthyridine, 2,7-naphthyridine, 1,7-phenanthroline, 1,8-phenanthroline, 1,9-phenanthroline,1,10-phenanthroline, indolizine, 4H-quinolizine, carboline, ergoline, purine, pteridine, alloxazine or flavin;

the expression "substituted" or substituent can be defined as follows: —H, —OH, —$R_a$, —O-alkyl, —O-aryl, —O-heteroaroyl, —O-heterocycle, —$NH_2$, —$NO_2$, —CN, —$N_3$, —$CNR_aNR_bR_c$, —$NR_aR_b$, $NR_aR_bR_c^+$, fluorine, chlorine, bromine, a-, b-, to w-amino acid esters, —$NR_aCOR_b$, —$NR_aCOXR_b$(X=—O, —NR, —$PO_{0,2,3,4}R$, —$SO_{0,1,2,4}R$, —$NR_aNR_bR_c$), —$COR_a$, —$COOR_a$, —$OCOOR_a$, —$OCONR_aR_b$, —$NR_cCONR_aR_b$, —$R_a$—O—$R_b$, —$R_c$—$NR_aR_b$, —$R_a$—S—$R_b$, —$R_a$—SO—$R_b$, —$R_a$—$S(O)_2$—$R_b$—$OR_a$—O—$R_b$, —$NR_aR_b$—O—$R_c$, —$SO_2R_a$, —$SO_{1,2,3,4}R_a$—O—$R_b$, —$COR_a$—$OR_b$, —$COOR_a$—O—$R_b$, —$OCOR_a$, —O—$R_b$, —$OCOOR_a$—O—$R_b$, —$NR_bCOR_a$—O—$R_b$, —$CONR_aR_b$—O—$R_c$, —$OCONR_aR_b$—O—$R_c$, —$NR_cCONR_aR_b$—O—$R_d$, —$NR_aCOR_b$—O—$R_c$, —$OR_a$—S—$R_b$, —$NR_aR_b$—S—$R_c$, —$SO_{1,2,3,4}R_a$—S—$R_b$, —$COR_a$—S—$R_b$, —$OCOR_a$—S—$R_b$, —$OCOR_a$—S—$R_b$, —$NR_aCOR_b$—S—$R_c$, —$CONR_aR_b$—S—$R_c$, —$NR_aCONR_bR_c$—S—$R_d$, —$OR_a$—$NR_bR_c$, —$NR_aR_b$—$NR_cR_d$, —$SO_{1,2,3,4}R_b$—$NR_bR_c$, —$COR_a$—$NR_bR_c$, —$COOR_a$—$NR_bR_c$, —$OCOR_a$—$NR_bR_c$, —$OCOOR_a$—$NR_bR_c$, —$NR_aCONR_bR_c$—$NR_dRe$, —$NR_aCOOR_b$—$NR_cR_d$, —$OCONR_aR_b$—$NR_cR_d$, —$NR_a$—$CONR_bR_c$—$NHR_d$, —$NR_aCOOR_b$—$NR_c$—$R_d$, —$POOR_aOR_b$, —$NR_cPOOR_aOR_b$, —$SO_2NR_aR_b$, —$SONR_aNR_bR_c$, —$SNR_aR_bNR_cR_d$, —$NR_aSO_2R_b$, —$NR_aSONR_bR_c$, —$NR_aSNR_bNR_cR_d$, —$NR_aSO_2NR_bRe$, —$NR_aSONR_bNR_cRd$ or —$NR_aSNR_bNR_cNR_dRe$, it being possible for the substituents to be, for example, bonded by way of a double bond or fused, wherein $R_a$, $R_b$, $R_c$ and $R_d$ may be, each independently of the others, in the form of substituents, as defined above, alkyl, alkenyl, alkynyl, aroyl, heteroaroyl, a heterocycle, aralkyl, aralkenyl or perhaloalkyl and or may be a member of a chain corresponding to alkylene, alkenylene, alkynylene, aroylene, heteroaroylene, heterocyclene, aralkylene, aralkenylene or perhaloalkylene; $R_a$, $R_b$, $R_c$ and $R_d$ may themselves be substituted, for example by alkyl, alkenyl, alkynyl, aroyl, heteroaroyl, a heterocycle, aralkyl, aralkenyl or perhalo-alkyl, the substituents of $R_a$, $R_b$, $R_c$ and $R_d$, however, being preferably unsubstituted; it being clear, in the above formulae, from the valency of the atoms to which $R_a$, $R_b$, $R_c$ and $R_d$ are bonded, when $R_a$, $R_b$, $R_c$ and $R_d$ are substituents or when they are chain members (for example, in —$COR_a$—$NR_bR_c$, $R_a$ is a chain member as carbon is at most tetravalent);

the expression "ring" can denote an aromatic, a cycloalkyl, cycloalkenyl, cycloalkynyl or heterocyclic ring.

The expression "heterocyclic ring" can denote, for example, a cycloalkyl, cycloalkenyl, cycloalkynyl or aromatic ring which, besides C atoms, contains $_{1, 2, 3}$ or 4 N, S or O atoms, with preference being given to 5- or 6-membered rings containing 1 or 2 N atoms.

The imidazole ring can be, for example, unsubstituted or can have, for example, 1, 2, 3 or 4, preferably 1, 2, or 3, substituent(s) selected from halogen atoms, pseudohalogens, substituted or unsubstituted alkyl, alkenyl, alkynyl, aralkyl, aralkenyl, aralkynyl, cycloalkyl, cycloalkenyl, cycloalkynyl, cycloaralkyl, cycloaralkenyl, cycloaralkynyl, aryl, alkoxy radicals and non-aromatic or aromatic or partially aromatic heterocyclic radicals, which may be unsubstituted or substituted by one or more substituent(s) selected from —OH, —$R_a$, —O-alkyl, —O-aryl, —O-heteroaroyl, an —O-heterocycle, —$NH_2$, —$NO_2$, —CN, —$N_3$, —$CNR_aNR_bR_c$, —$NR_aR_b$, $NR_aR_bR_c^+$, fluorine, chlorine, bromine, a-, b-, to w-amino acid esters, —$NR_aCOR_b$, —$NR_aCOXR_b$ (X=—O, —NR, —$PO_{0,2,3,4}R$, —$SO_{0,1,2,4}R$, —$NR_aNR_bR_c$), —$COR_a$, —$COOR_a$, —$OCOOR_a$, $CONR_aR_b$, —$OCONR_aR_b$, —$NR_cCONR_aR_b$, —$R_a$—O—$R_b$, —$R_c$—$NR_aR_b$, —$R_a$—S—$R_b$, —$R_a$—SO—$R_b$, —$R_a$—$S(O)_2$—$R_b$, —$OR_a$—O—$R_b$, —$NR_aR_b$—O—$R_c$, —$SO_2R_a$, —$SO_{1,2,3,4}R_a$—O—$R_b$, —$COR_a$—$OR_b$, —$COOR_a$—O—$R_b$, —$OCOR_a$—O—$R_b$, —$OCOOR_a$—O—$R_b$, —$NR_bCOR_aO$—$R_b$, —$CONR_aR_b$—O—$R_c$, —$OCONR_aR_b$—O—$R_c$, —$NR_cCONR_aR_b$—O—$R_d$, —$NR_aCOR_b$—O—$R_c$, —$OR_a$—S—$R_b$, —$NR_aR_b$—S—$R_c$, —$SO_{1,2,3,4}R_a$—S—$R_b$, —$COR_a$—S—$R_b$, —$OCOR_a$—S—$R_b$, —$OCOR_a$—S—$R_b$, —$NR_aCOR_b$—S—$R_c$, —$CONR_aR_b$—S—$R_c$, —$NR_aCONR_bR_c$—S—$R_d$, —$OR_a$—$NR_bR_c$, —$NR_aR_b$—$NR_cR_d$, —$SO_{1,2,3,4}R_b$—$NR_bR_c$, —$COR_a$—$NR_bR_c$, —$COOR_a$—$NR_bR_c$, —$OCOR_a$—$NR_bR_c$, —$OCOOR_a$—$NR_bR_c$, —$NR_aCONR_bR_c$—$NR_d$, —$NR_aCOOR_b$—$NR_cR_d$, —$OCONR_aR_b$—$NR_dR_d$, —$NR_aCONR_bR_c$—$NHR_d$, —$NR_aCOOR_b$—$NR_cR_d$, —$POOR_aOR_b$, —$NR_cPOOR_aOR_b$, —$SO_2NR_aR_b$, —$SONR_aNR_bR_c$, —$SNR_aR_bNR_cR_d$, —$NR_aSO_2R_b$, —$NR_aSONR_bR_c$, —$NR_aSNR_bNR_cR_d$, —$NR_aSO_2NR_b$, —$NR_aSONR_bNR_c$ and —$NR_aSNR_bNR_cNR_d$, wherein $R_a$, $R_b$, $R_c$ and $R_d$ may be, each independently of the others, in the form of substituents, as defined above, alkyl, alkenyl, alkynyl, aroyl, heteroaroyl, a heterocycle, aralkyl, aralkenyl or perhaloalkyl or may be a member of a chain corresponding to alkylene, alkenylene, alkynylene, aroylene, heteroaroylene, heterocyclene, aralkylene, aralkenylene or perhaloalkylene; $R_a$, $R_b$, $R_c$ and $R_d$ may themselves be substituted, for example by alkyl, alkenyl, alkynyl, aroyl, heteroaroyl, a hetero-cycle, aralkyl, aralkenyl or by perhaloalkyl, the substituents of $R_a$, $R_b$, $R_c$ and $R_d$, however, being preferably unsubstituted, it being possible for the substituents to be, for example, bonded by way of a double bond or fused.

Preference is given to the imidazole ring being bonded to atom X in formula I by way of its 5-position ring atom. Special preference is given to the imidazole ring having additional substituents in the 1- and/or 4-positions.

Specific examples of substituents on the imidazole ring are cyclohexyl, indanyl, tetrahydronaphthyl, benzylpiperidyl, benzyl, phenethyl, indolyl, methylindolyl, ethylindolyl, 5-(benzyloxy)-1H-pyrrolo[2,3-c]pyridyl, fluorophenyl.

Further preferred substituents can be found in the Examples.

Special preference is given to the imidazole ring being substituted in the 1-position by cycloalkyls having preferably 5, 6 or 7 ring atoms to which aryls or heteroaryls having preferably 5 or 6 ring atoms are fused. Especially preferred heteroaryls are furan and thiophene. The cycloalkyls, aryls and heteroaryls may have 1, 2, 3, 4 or 5 substituents, for example halogens, —$CF_3$, —OMe, —OH, —Me, with preference being given to compounds that are unsubstituted or that have one substituent.

According to a further preferred embodiment, the imidazole ring has, in addition to or alternatively to substitution in the 1-position, a substituent in the 4-position.

That substituent preferably consists of substituted or unsubstituted alkyls, heteroaryls or aryls, with preference being given to heteroaryls or aryls having 5 or 6 ring atoms.

Furthermore, the 3-pyrroloimidazole derivatives may have the following general formulae:

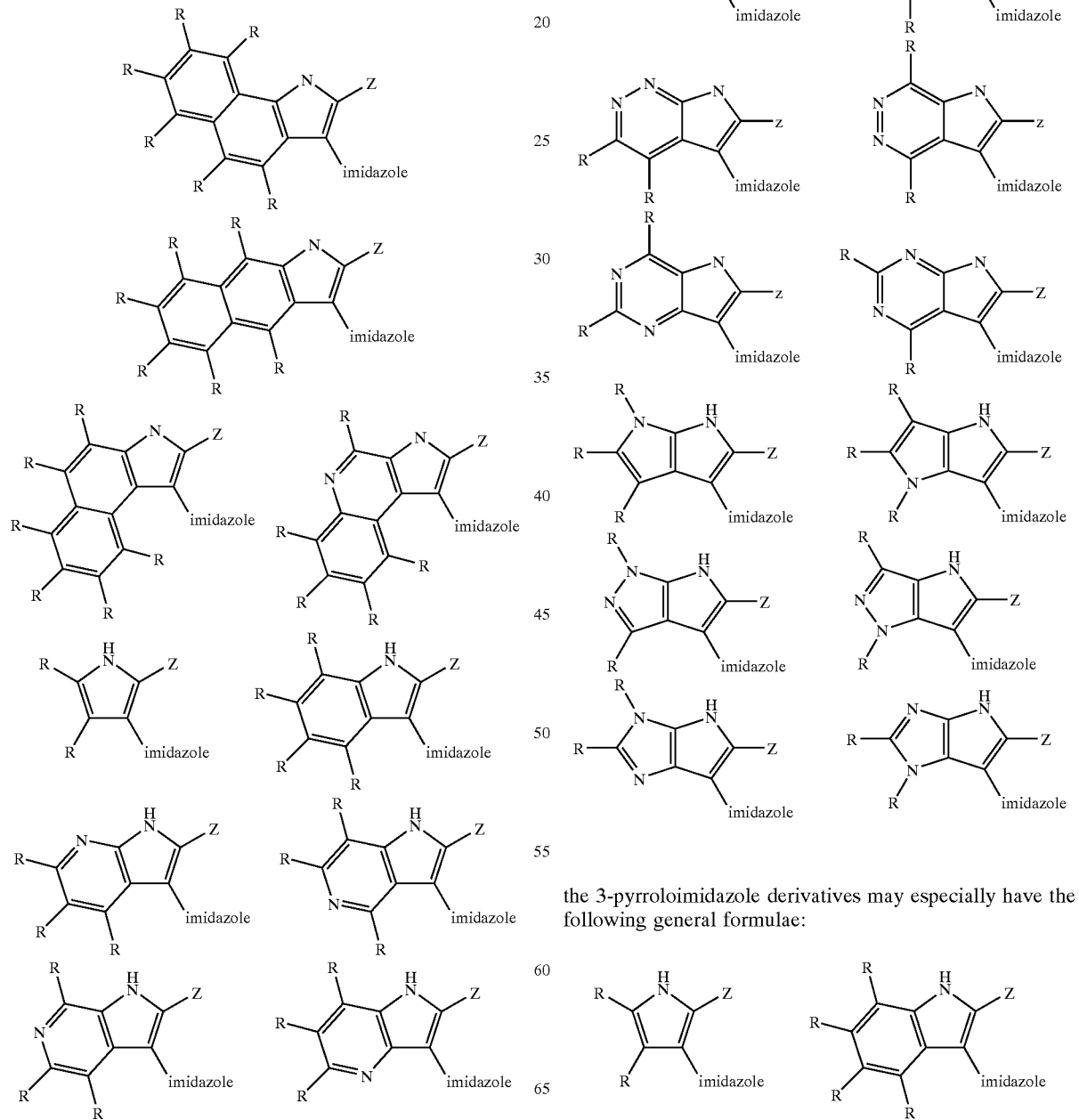

the 3-pyrroloimidazole derivatives may especially have the following general formulae:

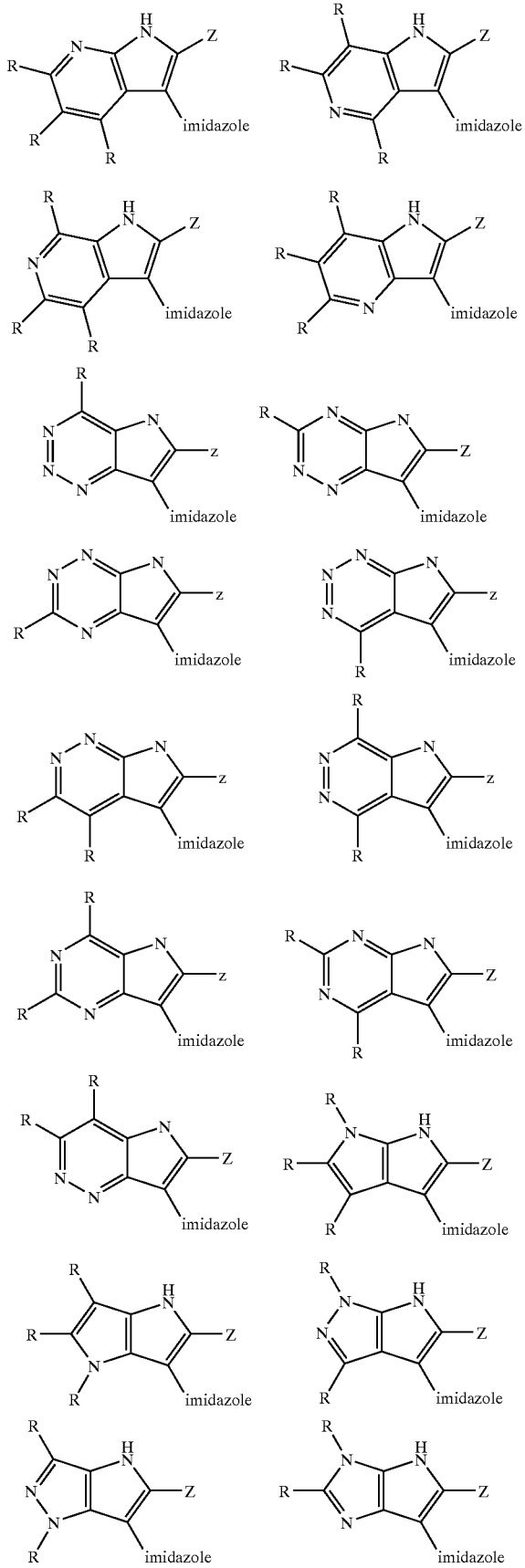

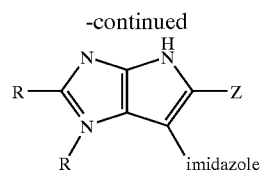

the 3-pyrroloimidazole derivatives may more especially have the following general formulae:

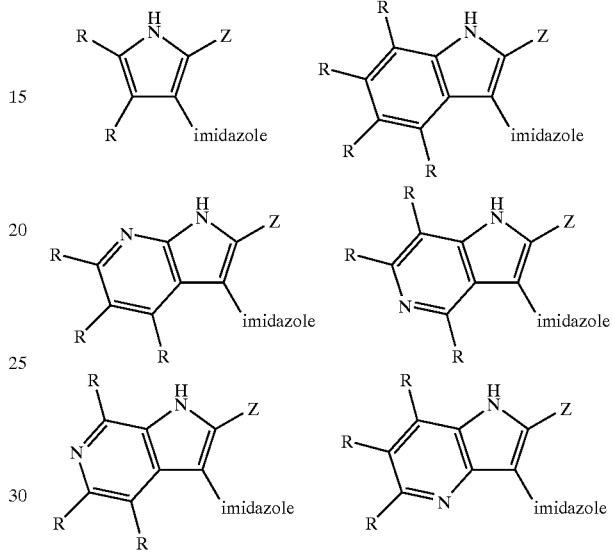

wherein the radicals Z are as defined hereinbefore and the radicals R are, each independently of the other(s), a hydrogen atom, a halogen atom, a pseudohalogen, an optionally substituted alkyl, alkenyl, alkynyl, aralkyl, aralkenyl, aralkynyl, cycloalkyl, cycloalkynyl, cycloaralkyl, cycloaralkenyl, cycloaralkynyl, aryl, aryloxy, aralkyloxy, alkoxy radical, a substituent or a heterocyclic ring, and/or two or more of the radicals R may form, for example a further ring. Preferably, the radicals R are, each independently of the other(s), a hydrogen atom, a halogen atom, a pseudohalogen, especially a hydrogen atom, fluorine, chlorine, bromine or iodine, more especially a hydrogen atom.

According to a preferred embodiment, compounds of formula I wherein X=Y=A=B=N are excluded. For example, 2 or 3 of the atoms X, Y, A and B may be N atoms; likewise, for example, 2 or 3 of the atoms X, Y, A and B may be C atoms.

Furthermore, pharmaceutical compositions are disclosed, in accordance with the invention, comprising at least one of the afore-mentioned compounds, optionally in combination with carriers and/or adjuvants and/or excipients customary per se.

The compounds according to the invention have a high level of activity, especially in cancer and tumour prophylaxis and therapy. That activity allows the active ingredients and pharmaceutical compositions according to the invention to be used as chemotherapeutic agents in human and veterinary medicine.

The term "chemotherapeutic agents" is a broad term encompassing substances having a (substantially) selectively damaging action on tumour cells and pathogens. The terms cytostatic agents and antibiotics are also widely used.

The antibiotic activity of the compounds and active ingredients according to the invention and of pharmaceutical compositions comprising them is especially pronounced. It will be clear that the term "antibiotic" is to be understood in its widest sense and encompasses, for example, antibacterial and antimycotic and/or antifungal action (including action against yeasts).

The compounds or pharmaceutical compositions according to the invention can be used locally or systemically. Systemic administration is understood to mean, for example, intravenous, intrapleural, intraperitoneal, rectal or oral administration or irrigation of body cavities and the urinary bladder. Local administration is understood to mean, for example, subcutaneous, intracutaneous, intratumoral or peritumoral administration, for example in the form of injection solutions, injection suspensions, creams, lotions, gels and ointments.

The life of tumour cells in vitro is significantly shortened by the active ingredients according to the invention compared to controls.

On systemic and local administration, the active ingredients according to the invention have a dose-dependent tumour-lysing action and an especially pronounced antibiotic action. When used therapeutically, the daily dose of active ingredients according to the invention is of the order of from 0.1 to 100 mg/kg of bodyweight, preferably from 2 to 40 mg/kg of bodyweight. In individual cases, the dosage may be higher or lower than that mentioned above.

The active ingredients according to the invention can be used in known manner—depending upon the individual clinical entity—in a formulation, for example patches, ointments, pastes, gels, creams, soluble powders, lotions, emulsions, sprays, powders, suspensions, suppositories and injection solutions.

The active ingredients according to the invention can be formulated, for example, as injection solutions, by dissolving them, where appropriate with the aid of solubilisers, in dilute physiologically acceptable bases and by being brought into an injectable form having a pH of from 6 to 8, especially from 6.9 to 7.5, by the addition of physiologically acceptable acids.

Examples of physiologically acceptable bases are hydroxides, hydrogen carbonates, carbonates of alkali and alkaline-earth metals, especially of potassium, sodium and calcium.

Examples of physiologically acceptable acids are lactic acid, citric acid, tartaric acid, oxalic acid, malic acid, acetic acid, formic acid, benzoic acid, salicylic acid, hydrochloric acid, sulphuric acid or phosphoric acid.

Excipients may be mixed in with the formulation of active ingredients according to the invention (one or more of which may be used). Such non-toxic and pharmaceutically suitable excipients may be, for example, solid, semi-solid or liquid carriers, emulsifiers or dispersants, preservatives, anti-oxidants, UV absorbers. The concentration of active ingredients according to the invention is from 1 to 90% by weight, preferably from 5 to 50% by weight.

The dosage units of the active ingredients according to the invention may consist of, for example, 1, 2, 3 or 4 individual doses or ½, ⅓ or ¼ of an individual dose. An individual dose preferably contains the amount of active ingredient given on one administration, which usually corresponds to all, a half or a third or even a quarter of a daily dose.

Creams, pastes, ointments and gels may comprise, beside the active ingredient(s), carriers known to the person skilled in the art, for example waxes, paraffins, starches, vegetable and animal fats, cellulose derivatives, tragacanth, silicic acid, talcum, zinc oxide, bentonites, silicones, polyethylene glycols.

Sprays and powders may comprise, besides the active ingredient(s), carriers known to the person skilled in the art, for example lactose, talcum, silicic acid, aluminium hydroxide, calcium silicate or polyamide powder or mixtures thereof. Sprays may comprise, in addition, propellants, for example chlorofluorocarbons.

Suppositories may comprise, besides the active ingredients, carriers known to the person skilled in the art, for example polyethylene glycols, fats or mixtures thereof.

The present invention relates also to antibody conjugates comprising one or more tumour-specific antibodies and one or more active ingredients according to the invention, which can be cleaved under tumour-specific physiological conditions in the area surrounding the tumour or in the interior of the tumour. Those antibody conjugates may be packed in liposomes.

Local administration of the active ingredients according to the invention may be carried out by means of micro-machines.

In order to obtain better, locally relevant active ingredient concentrations and for greater tolerability, the active ingredients according to the invention may be packed in liposomes.

If advantageous for treatment of the tumour disease or infection or for the general condition of the patient or of the patient's family, combinations with other active ingredients of use to the patient may be administered simultaneously or at different times.

The present invention also encompasses the use of the described active ingredients and pharmaceutical compositions comprising one or more active ingredients for the purpose of treating atypical tissues, in humans and livestock, that hinder or interfere with the course of normal biological functions.

Such tissues may be, for example:

benign and malignant tumours that are solid or cystic in nature, adenomas, cystadenomas, papillomas, adeno-carcinonmas including those of the cirrhotic type, basal cell carcinomas, sarcomas, for example fibrosarcoma, liposarcoma, lympho-sarcoma, rhabdomyosarcoma, myxosarcoma, chondrosarcoma, reticulum cell sarcoma, Hodgkin's disease, embryonal tumours, for example neuroblastoma, nephroblastoma, teratoma, adamantinoma, retroblastoma, haemangioma, chordoma, odontoma, craniopharyngoma, hamartomas, for example lymphoangioma, exostoses, neurofibrantosis, melanomas, lymphomas, hepatoblastomas, mammary carcinomas, cervical carcinoma, choriocarcinoma, adenoacanthoma, androblastoma, leiomyoma, arrhenoblastoma, Sertoli's cell tumour, theca and granulosa cell tumour, germi-noma and seminoma, ovarian and vulvar carcinoma, urinary bladder and prostate carcinoma, tumours caused by schistosomiasis, astrocytoma, ependymogliomas, glioblastomas, medulloblastoma, oligodendroglioma, spongio-blastoma, meningeoma and also tumours of Schwann's sheath cells, pinealoma, haemangioblastoma, osteoclastoma, Ewing's tumour, multiple myeloma, mycosis fungoides, Burkitt's tumour, leukaemias, for example acute and chronic lymphatic leukaemia, acute and chronic granulocytic leukaemia, acute and chronic monocytic leukaemia and also stem cell leukaemia, basalioma, fibroma, myoma and also metastases of any form of tumour that are accessible by surgical intervention in the form of a local injection.

Specific examples of pyrroloimidazole derivatives according to the invention that may be mentioned are:

3-(1-cyclohexyl-1H-imidazol-5-yl)-1-methyl-1H-indole

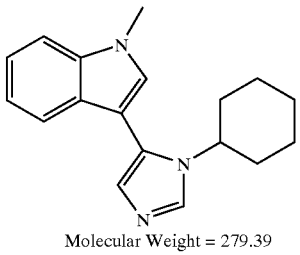

Molecular Weight = 279.39
Molecular Formula = C18H21N3

[M+H]+. Found ISP-TOF-MS: 279.3882 [M+H]+; 302.3782 [M+Na]+.

5-(benzyloxy)-3-(1-cyclohexyl-1H-imidazol-5-yl)-1H-pyrrolo[2,3-c]pyridine

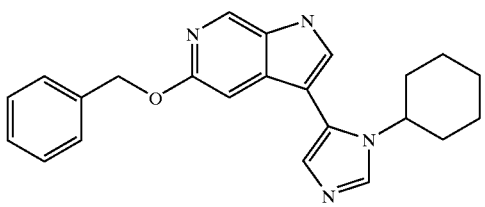

Molecular Weight = 372.47
Molecular Formula = C23H24N4O

[M+H]+. Found ISP-TOF-MS: 373.4739 [M+H]+; 395.4639 [M+Na]+.

3-(1-cyclohexyl-1H-imidazol-5-yl)-1H-indole

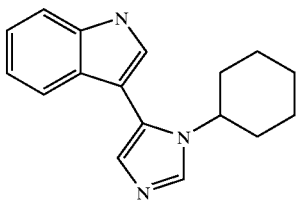

Molecular Weight = 265.36
Molecular Formula = C17H19N3

[M+H]+. Found ISP-TOF-MS: 266.3610 [M+H]+; 288.3511 [M+Na]+.

1. 5-Benzyloxy-3-[3-(5-chloro-1,2,3,4-tetrahydro-naphth-1-yl)-3H-imidazol-4-yl]-1H-pyrrolo[2,3-c]pyridine
2. 5-Benzyloxy-3-[3-(6-chloro-1,2,3,4-tetrahydro-naphth-1-yl)-3H-imidazol-4-yl]-1H-pyrrolo[2,3-c]pyridine
3. 5-Benzyloxy-3-[3-(7-chloro-1,2,3,4-tetrahydro-naphth-1-yl)-3H-imidazol-4-yl]-1H-pyrrolo[2,3-c]pyridine
4. 5-Benzyloxy-3-[3-(8-chloro-1,2,3,4-tetrahydro-naphth-1-yl)-3H-imidazol-4-yl]-1H-pyrrolo[2,3-c]pyridine
5. 5-Benzyloxy-3-[3-(5,8-dichloro-1,2,3,4-tetrahydro-naphth-1-yl)-3H-imidazol-4-yl]-1H-pyrrolo[2,3-c]pyridine
6. 5-Benzyloxy-3-[3-(5,7-dichloro-1,2,3,4-tetrahydro-naphth-1-yl)-3H-imidazol-4-yl]-1H-pyrrolo[2,3-c]pyridine
7. 5-Benzyloxy-3-[3-(5,6-dichloro-1,2,3,4-tetrahydro-naphth-1-yl)-3H-imidazol-4-yl]-1H-pyrrolo[2,3-c]pyridine
8. 5-Benzyloxy-3-[3-(6,8-dichloro-1,2,3,4-tetrahydro-naphth-1-yl)-3H-imidazol-4-yl]-1H-pyrrolo[2,3-c]pyridine
9. 5-Benzyloxy-3-[3-(7,8-dichloro-1,2,3,4-tetrahydro-naphth-1-yl)-3H-imidazol-4-yl]-1H-pyrrolo[2,3-c]pyridine
10. 5-Benzyloxy-3-[5-methyl-3-(5-chloro-1,2,3,4-tetrahydro-naphth-1-yl)-3H-imidazol-4-yl]-1H-pyrrolo[2,3-c]pyridine
11. 5-Benzyloxy-3-[5-methyl-3-(5-chloro-1,2,3,4-tetrahydro-naphth-1-yl)-3H-imidazol-4-yl]-1H-pyrrolo[2,3-c)pyridine
12. 5-Benzyloxy-3-[5-methyl-3-(6-chloro-1,2,3,4-tetrahydro-naphth-1-yl)-3H-imidazol-4-yl]-1H-pyrrolo[2,3-c)pyridine
13. 5-Benzyloxy-3-[5-methyl-3-(7-chloro-1,2,3,4-tetrahydro-naphth-1-yl)-3H-imidazol-4-yl]-1H-pyrrolo[2,3-c]pyridine
14. 5-Benzyloxy-3-[5-methyl-3-(8-chloro-1,2,3,4-tetrahydro-naphth-1-yl)-3H-imidazol-4-yl]-1H-pyrrolo[2,3-c]pyridine
15. 5-Benzyloxy-3-[5-methyl-3-(5,8-dichloro-1,2,3,4-tetrahydro-naphth-1-yl)-3H-imidazol-4-yl]-1H-pyrrolo[2,3-c]pyridine
16. 5-Benzyloxy-3-[5-methyl-3-(5,7-dichloro-1,2,3,4-tetrahydro-naphth-1-yl)-3H-imidazol-4-yl]-1H-pyrrolo[2,3-c]pyridine
17. 5-Benzyloxy-3-[5-methyl-3-(5,6-dichloro-1,2,3,4-tetrahydro-naphth-1-yl)-3H-imidazol-4-yl]-1H-pyrrolo[2,3-c]pyridine
18. 5-Benzyloxy-3-[5-methyl-3-(6,8-dichloro-1,2,3,4-tetrahydro-naphth-1-yl)-3H-imidazol-4-yl]-1H-pyrrolo[2,3-c]pyridine
19. 5-Benzyloxy-3-[5-methyl-3-(7,8-dichloro-1,2,3,4-tetrahydro-naphth-1-yl)-3H-imidazol-4-yl]-1H-pyrrolo[2,3-c]pyridine
20. 5-Benzyloxy-3-[5-isopropyl-3-(1,2,3,4-tetrahydro-naphth-1-yl)-3H-imidazol-4-yl]-1H-pyrrolo[2,3-c]pyridine
21. 5-Benzyloxy-3-[5-isopropyl-3-(5-chloro-1,2,3,4-tetrahydro-naphth-1-yl)-3H-imidazol-4-yl]-1H-pyrrolo[2,3-c]pyridine
22. 5-Benzyloxy-3-[5-isopropyl-3-(6-chloro-1,2,3,4-tetrahydro-naphth-1-yl)-3H-imidazol-4-yl]-1H-pyrrolo[2,3-c]pyridine
23. 5-Benzyloxy-3-[5-isopropyl-3-(7-chloro-1,2,3,4-tetrahydro-naphth-1-yl)-3H-imidazol-4-yl]-1H-pyrrolo[2,3-c]pyridine
24. 5-Benzyloxy-3-[5-isopropyl-3-(8-chloro-1,2,3,4-tetrahydro-naphth-1-yl)-3H-imidazol-4-yl]-1H-pyrrolo[2,3-c]pyridine
25. 5-Benzyloxy-3-[5-isopropyl-3-(5,8-dichloro-1,2,3,4-tetrahydro-naphth-1-yl)-3H-imidazol-4-yl]-1H-pyrrolo[2,3-c]pyridine
26. 5-Benzyloxy-3-[5-isopropyl-3-(5,7-dichloro-1,2,3,4-tetrahydro-naphth-1-yl)-3H-imidazol-4-yl]-1H-pyrrolo[2,3-c]pyridine
27. 5-Benzyloxy-3-[5-isopropyl-3-(6,8-dichloro-1,2,3,4-tetrahydro-naphth-1-yl)-3H-imidazol-4-yl]-1H-pyrrolo[2,3-c]pyridine
28. 5-Benzyloxy-3-[5-isopropyl-3-(7,8-dichloro-1,2,3,4-tetrahydro-naphth-1-yl)-3H-imidazol-4-yl]-1H-pyrrolo[2,3-c]pyridine
29. 1-[5-(5-Benzyloxy-1H-pyrrolo[2,3-c]pyrid-3-yl)-1-(1,2,3,4-tetrahydro-naphth-1-yl)-1H-imidazol-4-yl]-ethanol
30. 1-[5-(5-Benzyloxy-1H-pyrrolo[2,3-c]pyrid-3-yl)-1-(6-chloro-1,2,3,4-tetrahydro-naphth-1-yl)-1H-imidazol-4-yl]-ethanol
31. 1-[5-(5-Benzyloxy-1H-pyrrolo[2,3-c]pyrid-3-yl)-1-(7-chloro-1,2,3,4-tetrahydro-naphth-1-yl)-1H-imidazol-4-yl]-ethanol
32. 1-[5-(5-Benzyloxy-1H-pyrrolo[2,3-c]pyrid-3-yl)-1-(8-chloro-1,2,3,4-tetrahydro-naphth-1-yl)-1H-imidazol-4-yl]-ethanol
33. 1-[5-(5-Benzyloxy-1H-pyrrolo[2,3-c]pyrid-3-yl)-1-(5,8-dichloro-1,2,3,4-tetrahydro-naphth-1-yl)-1H-imidazol-4-yl]-ethanol
34. 1-[5-(5-Benzyloxy-1H-pyrrolo[2,3-c]pyrid-3-yl)-1-(5,7-dichloro-1,2,3,4-tetrahydro-naphth-1-yl)-1H-imidazol-4-yl]-ethanol
35. 1-[5-(5-Benzyloxy-1H-pyrrolo[2,3-c]pyrid-3-yl)-1-(7,8-dichloro-1,2,3,4-tetrahydro-naphth-1-yl)-1H-imidazol-4-yl]ethanol
36. 1-[5-(5-Benzyloxy-1H-pyrrolo[2,3-c]pyrid-3-yl)-1-(6,8-dichloro-1,2,3,4-tetrahydro-naphth-1-yl)-1H-imidazol-4-yl]-ethanol
37. 1-[5-(5-Benzyloxy-1H-pyrrolo[2,3-c]pyrid-3-yl)-1-(5-chloro-1,2,3,4-tetrahydro-naphth-1-yl)-1H-imidazol-4-yl]-ethanol
38. 2-[5-(5-Benzyloxy-1H-pyrrolo[2,3-c]pyrid-3-yl)-1-(1,2,3,4-tetrahydro-naphth-1-yl)-1H-imidazol-4-yl]-ethanol
39. 2-[5-(5-Benzyloxy-1H-pyrrolo[2,3-c]pyrid-3-yl)-1-(5-chloro-1,2,3,4-tetrahydro-naphth-1-yl)-1H-imidazol-4-yl]-ethanol
40. 2-[5-(5-Benzyloxy-1H-pyrrolo[2,3-c]pyrid-3-yl)-1-(6-chloro-1,2,3,4-tetrahydro-naphth-1-yl)-1H-imidazol-4-yl]-ethanol
41. 2-[5-(5-Benzyloxy-1H-pyrrolo[2,3-c]pyrid-3-yl)-1-(7-chloro-1,2,3,4-tetrahydro-naphth-1-yl)-1H-imidazol-4-yl]-ethanol
42. 2-[5-(5-Benzyloxy-1H-pyrrolo[2,3-c]pyrid-3-yl)-1-(8-chloro-1,2,3,4-tetrahydro-naphth-1-yl)-1H-imidazol-4-yl]-ethanol
43. 2-[5-(5-Benzyloxy-1H-pyrrolo[2,3-c]4-pyrid-3-yl)-1-(5,8-dichloro-1,2,3,4-tetrahydro-naphth-1-yl)-1H-imidazol-4-yl]-ethanol
44. 2-[5-(5-Benzyloxy-1H-pyrrolo[2,3-c]pyrid-3-yl)-1-(6,8-dichloro-1,2,3,4-tetrahydro-naphth-1-yl)-1H-imidazol-4-yl]-ethanol
45. 2-[5-(5-Benzyloxy-1H-pyrrolo[2,3-c]pyrid-3-yl)-1-(7,8-dichloro-1,2,3,4-tetrahydro-naphth-1-yl)-1H-imidazol-4-yl]ethanol
46. 2-[5-(5-Benzyloxy-1H-pyrrolo[2,3-c]pyrid-3-yl)-1-(5,7-dichloro-1,2,3,4-tetrahydro-naphth-1-yl)-1H-imidazol-4-yl]-ethanol
47. 5-Benzyloxy-3-[3-(4,5,6,7-tetrahydro-benzo[b]thiophen-4-yl)-3H-imidazol-4-yl]-1H-pyrrolo[2,3-c]pyridine

| | |
|---|---|
| 48 | 5-Benzyloxy-3-[3-(4,5,6,7-tetrahydro-benzofuran-4-yl)-3H-imidazol-4-yl]-1H-pyrrolo[2,3-c]pyridine |
| 49 | 5-Benzyloxy-3-[3-(6,7,8,9-tetrahydro-5H-benzocyclohepten-5-yl)-3H-imidazol-4-yl]-1H-pyrrolo(2,3-c)pyridine |
| 50 | 5-Benzyloxy-3-[3-(6,7,8,9-tetrahydro-5H-benzocyclohepten-6-yl)-3H-imidazol-4-yl]-1H-pyrrolo[2,3-c]pyridine |
| 51 | 5-(4-Chloro-benzyloxy)-3-[3-(1,2,3,4-tetrahydro-naphth-1-yl)-3H-imidazol-4-yl]-1H-pyrrolo[2,3-c]pyridine |
| 52 | 5-(2,4-Dichloro-benzyloxy)-3-[3-(1,2,3,4-tetrahydro-naphth-1-yl)-3H-imidazol-4-yl]-1H-pyrrolo[2,3-c]pyridine |
| 53 | 5-(3-Chloro-benzyloxy)-3-[3-(1,2,3,4-tetrahydro-naphth-1-yl)-3H-imidazol-4-yl]-1H-pyrrolo[2,3-c]pyridine |
| 54 | 5-(2-Chloro-benzyloxy)-3-[3-(1,2,3,4-tetrahydro-naphth-1-yl)-3H-imidazol-4-yl]-1H-pyrrolo[2,3-c]pyridine |
| 55 | 5-(2,3-Chloro-benzyloxy)-3-[3-(1,2,3,4-tetrahydro-naphth-1-yl)-3H-imidazol-4-yl]-1H-pyrrolo[2,3-c]pyridine |
| 56 | 5-(2,5-Chloro-benzyloxy)-3-[3-(1,2,3,4-tetrahydro-naphth-1-yl)-3H-imidazol-4-yl]-1H-pyrrolo[2,3-c]pyridine |
| 57 | 5-(2,6-Chloro-benzyloxy)-3-[3-(1,2,3,4-tetrahydro-naphth-1-yl)-3H-imidazol-4-yl]-1H-pyrrolo[2,3-c]pyridine |
| 58 | 5-(4-Chloro-benzyloxy)-3-[3-(5-chloro-1,2,3,4-tetrahydro-naphth-1-yl)-3H-imidazol-4-yl]-1H-pyrrolo[2,3-c]pyridine |
| 59 | 3-[3-(5-Chloro-1,2,3,4-tetrahydro-naphth-1-yl)-3H-imidazol-4-yl]-5-(2,4-dichloro-benzyloxy)-1H-pyrrolo[2,3-c]pyridine |
| 60 | 5-(2,4-Dichloro-benzyloxy)-3-[3-(5,8-dichloro-1,2,3,4-tetrahydro-naphth-1-yl)-3H-imidazol-4-yl]-1H-pyrrolo[2,3-c]pyridine |
| 61 | 3-[3-(8-Chloro-1,2,3,4-tetrahydro-naphth-1-yl)-3H-imidazol-4-yl]-5-(2,4-dichloro-benzyloxy)-1H-pyrrolo[2,3-c]pyridine |
| 62 | 5-Benzyloxy-3-[3-(8-chloro-5-methoxy-1,2,3,4-tetrahydro-naphth-1-yl)-3H-imidazol-4-yl]-1H-pyrrolo[2,3-c]pyridine |
| 63 | 5-Benzyloxy-3-[3-(5-chloro-8-methoxy-1,2,3,4-tetrahydro-naphth-1-yl)-3H-imidazol-4-yl]-1H-pyrrolo[2,3-c]pyridine |
| 64 | 8-[5-(5-Benzyloxy-1H-pyrrolo[2,3-c]pyrid-3-yl)-imidazol-1-yl]4-chloro-5,6,7,8-tetrahydro-naphth-1-ol |
| 65 | 3-[3-(5-Chloro-1,2,3,4-tetrahydro-naphth-1-yl)-3H-imidazol-4-yl]-1H-pyrrolo[2,3-c]pyridin-5-ol |
| 66 | 5-Benzyloxy-3-[5-cyclopropyl-3-(1,2,3,4-tetrahydro-naphth-1-yl)-3H-imidazol-4-yl]-1H-pyrrolo[2,3-c]pyridine |
| 67 | 5-Benzyloxy-3-[5-cyclopropyl-3-(5-morpholin-4-yl-1,2,3,4-tetrahydro-naphth-1-yl)-3H-imidazol-4-yl]-1H-pyrrolo[2,3-c]pyridine |
| 68 | 3-[5-Cyclopropyl-3-(1,2,3,4-tetrahydro-naphth-1-yl)-3H-imidazol-4-yl]-5-methoxy-1H-pyrrolo[2,3-c]pyridine |

The compounds according to the invention are prepared in a manner customary per se, for example in accordance with van Leussen et al., J. Org. Chem., 42, 1977, 1153–1159.

By way of example, a general procedure for the synthesis of 1,5-disubstituted imidazole derivatives (Examples 1–2) is described below:

6 mmol of amine and 6 mmol of aldehyde are pre-condensed in 3 ml of dichloromethane overnight to form the Schiff's base, the dichloromethane is drawn off and 3 ml of methanol are added to the residue. To the resulting suspension there are added 6 mmol of solid TOSMIC and 1 equivalent of base and the mixture is boiled under reflux at 80° C. for four hours. The solvent is drawn off and the crude product is purified by means of preparative HPLC.

EXAMPLE 1

5-(Benzyloxy)-3-(1-tetrahydronaphthalene-1H-imidazol-5-yl)-1H-pyrrolo[2,3-c]pyridine

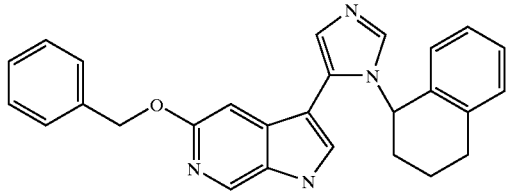

Molecular Weight = 420.52
Exact Mass = 420
Molecular Formula = C27H24N4O

Analytical Data $^1$H-NMR (CDCl$_3$, 400 MHz): δ=1.26 (m, 1H,), 1.70 (m, 1H, 1.86–2.08 (m, 4H, 2 CH$_2$); 2.72–2.88 (m, 1H, CH); 5.35 (s, 2H, O—CH$_2$); 6.91–7.46 (m, 13H, imidazole, 1H, phenyl, 5H, tetrahydronaphthyl, 4H, pyrrolopyridine 2H); 8.43 (s, 1H, imidazole 1H); 10.26 (d, 1H, pyrrolopyridine NH)

HPLC-MS (YMC ODS-A, 5 cm, 2μ, acetonitrile/water; API-ES): 2.81 min. 421.1 C$_{27}$H$_{24}$N$_4$O=420.52

Biological data

| Inhibition of bacterial growth: | | |
|---|---|---|
| Staph. aureus | c = 100 μM | 100% inhibition |
| Bac. subtilis | c = 100 μM | 100% inhibition |
| Strept. pneumoniae | c = 100 μM | 100% inhibition |
| Candida albicans | c = 100 μM | 0% inhibition |
| Cytotoxicity L50: | | |
| A549 | >100 μM | |
| HepG2 | >100 μM | |
| Cell proliferation GI50: A549 | >100 μM | 22% inhibition |

Example 2

3-(4-Benzylpiperidin-1H-imidazol-5-yl)-2-methyl-1H-indole

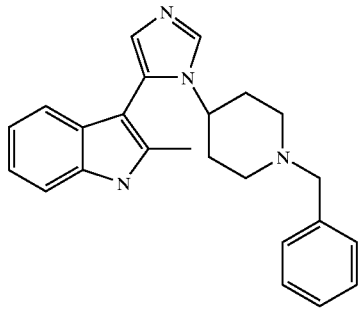

Molecular Weight = 370.50
Exact Mass = 370
Molecular Formula = C24H26N4

Analytical Data $^1$H-NMR (CD3OD, 400 MHz): δ=1.97 (s, 3H, CH$_3$); 2.31 (m, 8H, CH$_2$); 3.72 (s, 2H, CH$_2$); 6.99–7.54 (m, 11H, indole, imidazole, phenyl)

HPLC-MS (YMC ODS-A, 5 cm, 2μ, acetonitrile/water; API-ES): 0.59 min. 371.2 $C_{24}H_{26}N_4$=370.50

Biological Data

| Inhibition of bacterial growth: | | |
| --- | --- | --- |
| Staph. aureus | c = 100 μM | 100% inhibition |
| Bac. subtilis | c = 100 μM | 100% inhibition |
| Strept. pneumoniae | c = 100 μM | 90% inhibition |
| Candida albicans | c = 100 μM | 60% inhibition |
| Cytotoxicity L50: | | |
| A549 | >100 μM | |
| HepG2 | >100 μM | |
| Cell proliferation GI50: | | |
| A549 | >100 μM | 12% inhibition |
| HepG2 | >100 μM | 1% inhibition |

Growth-inhibiting, Cytotoxic and Antibiotic Properties

Assay 1

Measurement of cell growth by determination of the activity of the intracellular enzyme acid phosphatase. The added substrate p-nitrophenyl phosphate is converted by acid phosphatase into p-nitrophenol, which absorbs light at 405 nm, the intensity of the yellow coloration being proportional to the number of cells. Incubation of the cell lines HEPG-2 and A549 together with the substance (0.1–100 μM) was carried out for 48 h and 96 h at 37° C. and 5% $CO_2$.

Assay 2

Measurement of Cytotoxicity by Quantitative determination of the enzyme lactate dehydrogenase (LDH), a stable cytosolic enzyme that is released into the medium on lysis of the cell. Released LDH is measured by means of a coupled enzyme assay wherein a tetrazolium salt is converted into a red formazan product which can be detected at 490 nm, the amount of colour generated being proportional to the number of lysed cells. Incubation of the cell line HEPG2 and A549 together with the substance (0.1–100 μM) was carried out for 24 h at 37° C. and 5% $CO_2$.

Inhibition Test

Culture media used: Müller-Hinton broth Caso agar plates

Test method: Microdilution assay

The test organisms are cultured overnight in Müiller-Honton broth at 35° C. +/–2° C. The suspension of organisms is centrifuged (5000 rev./min, 4° C.); the pellet is resuspended in fresh medium and incubated for a further 2 h. The pellet is then resuspended in 0.9% NaCl solution and the number of cells is adjusted to about $10^8$ CFU/ml using standard curves. The resulting suspension is then diluted with Müller-Hinton broth to about $10^4$ CFU/ml(=inoculum).

Starting from the inoculum, a determination of the number of organisms is carried out by spiralling out (2×0.1 ml) a suitable dilution stage onto CASO agar plates.

Test procedure: Specific concentrations of the potential inhibitors are dispensed into a 96-well microtitre assay plate, wells A1–H1remaining empty. The wells of the microtitre assay plates are inoculated with the adjusted suspension of organisms. Wells A1–H1serve as growth controls. Immediately after inoculation and after incubation of the plates for 24 h and 48 h, they are measured in a plate reader (Biotek EL 311) at 550 nm. From the crude data, the inhibition of bacterial and fungal growth is calculated in percent.

General Synthesis of the Compounds in a 96-well Format (Examples 3–9)

200 μl of a 1M amine solution in dichloromethane, 200 μl of a 1M aldehyde solution in dichloromethane and 1 equivalent of $Et_3N$ are added directly to each well. The reaction mixture is shaken overnight without being covered. The residue formed is taken up in 200 μl of MeOH; 200 μl of 2M TOSMIC solution in methanol. The plate is closed using a Santoprene dimpled mat (Zinsser Analytic GmbH, Frankfurt) and an additional Teflon mat and is screwed tight. The aluminium block is heated at 80° C. for 4 h. The block is then allowed to cool and the reaction vessels are opened with caution.

The solvent is evaporated off overnight. The residue is taken up in 600 μl of ethyl acetate (EA) and 300 μl of water are added. With the aid of a PP plastic mat, the EA phase is shaken three times with 300 μl of water for the purpose of extraction. The aqueous phase is, in each case, drawn off and collected in a further "deep-well" plate. In order to remove the remaining remnants of water, a spatula tip of sodium sulphate is added to the EA phase and shaken. The EA phase is drawn off and the salt is rinsed with 100 μl. Then 2 amounts, each of 100 μl, of 2N hydrochloric acid are added and shaken for the purpose of extraction. The aqueous phase is collected in a further plate. That further plate then contains the purified imidazole derivative, which is in the form of its hydrochloride.

EXAMPLE 3

3-(4-Benzylpiperidin-1H-imidazol-5-yl)-1H-indole

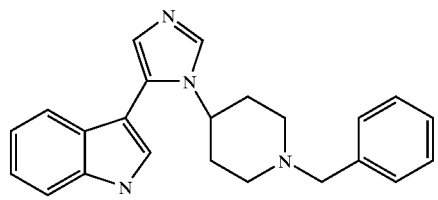

Molecular Weight = 356.47
Exact Mass = 356
Molecular Formula = C23H24N4

Analytical Data

HPLC-MS (YMC ODS-A, 5 cm, 2μ, acetonitrile/water; API-ES): 0.8 min. 357.2 $C_{231}H_{24}N_4$=356.47

Biological Data

| Inhibition of bacterial growth: | | |
| --- | --- | --- |
| Staph. aureus | c = 100 μM | 100% inhibition |
| Bac. subtilis | c = 100 μM | 100% inhibition |
| Strept. pneumoniae | c = 100 μM | 80% inhibition |
| Candida albicans | c = 100 μM | 60% inhibition |
| Cytotoxicity L50: | | |
| A549 | >100 μM | |
| HepG2 | >100 μM | |
| Cell proliferation GI50: | | |
| A549 | >100 μM | 26% inhibition |
| HepG2 | >100 μM | 48% inhibition |

EXAMPLE 4

5-(Benzyloxy)-3-(4-benzylpiperidin-1H-imidazol-5-yl)-1H-pyrrolo[2,3-c]pyridine

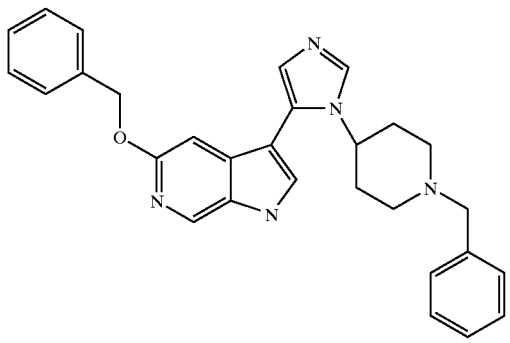

Molecular Weight = 463.59
Exact Mass = 463
Molecular Formula = C29H29N5O

Analytical Data

HPLC-MS (YMC ODS-A, 5 cm, $2\mu$, acetonitrile/water; API-ES): 0.85 min. 464.2 $C_{29}H_{29}N_5O$=463.59

Biological Data

| Inhibition of bacterial growth: | | |
|---|---|---|
| Staph. aureus | c = 100 $\mu$M | 100% inhibition |
| Bac. subtilis | c = 100 $\mu$M | 100% inhibition |
| Strept. pneumoniae | c = 100 $\mu$M | 90% inhibition |
| Candida albicans | c = 100 $\mu$M | 70% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 41% inhibition |
| HepG2 | >100 $\mu$M | 65% inhibition |

EXAMPLE 5

5-(Benzyloxy)-3-(1-(3-methyl-butyl)-1H-imidazol-5-yl)-1H-pyrrolo[2,3-c]pyridine

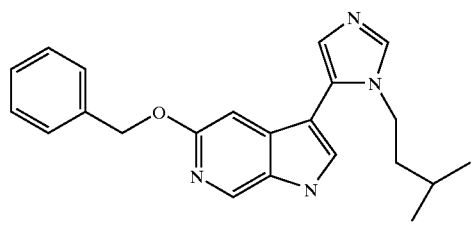

Molecular Weight = 360.46
Exact Mass = 360
Molecular Formula = C22H24N4O

Analytical Data

HPLC-MS (YMC ODS-A, 5 cm, $2\mu$, acetonitrile/water; API-ES): 2.65 min. 361.2 $C_{22}H_{24}N_4O$=360.46

Biological Data

| Inhibition of bacterial growth: | | |
|---|---|---|
| Staph. aureus | c = 100 $\mu$M | 100% inhibition |
| Bac. subtilis | c = 100 $\mu$M | 100% inhibition |
| Strept. pneumoniae | c = 100 $\mu$M | 90% inhibition |
| Candida albicans | c = 100 $\mu$M | 0% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 33% inhibition |
| HepG2 | >100 $\mu$M | 38% inhibition |

EXAMPLE 6

5-(Benzyloxy)-3-(1-(3-ethylindol)-1H-imidazol-5-yl)-1H-pyrrolo[2,3-c]pyridine

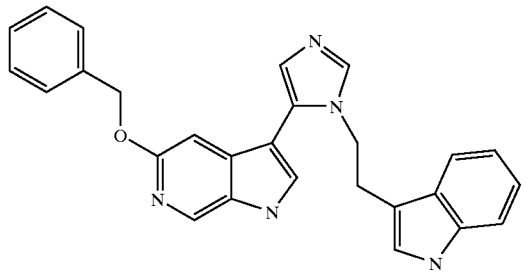

Molecular Weight = 433.52
Exact Mass = 433
Molecular Formula = C27H23N5O

Analytical Data

HPLC-MS (YMC ODS-A, 5 cm, $2\mu$, acetonitrile/water; API-ES): 2.46 min. 434.2 $C_{27}H_{23}N_5O$=433.52

Biological Data

| Inhibition of bacterial growth: | | |
|---|---|---|
| Staph. aureus | c = 100 $\mu$M | 85% inhibition |
| Bac. subtilis | c = 100 $\mu$M | 10% inhibition |
| Strept. pneumoniae | c = 100 $\mu$M | 10% inhibition |
| Candida albicans | c = 100 $\mu$M | 0% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 19% inhibition |
| HepG2 | >100 $\mu$M | 17% inhibition |

EXAMPLE 7

3-(1-(1,2,3,4-Tetrahydronaphthyl)-1H-imidazol-5-yl)-2-methyl-1H-indole

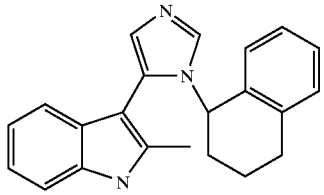

Molecular Weight = 327.43
Exact Mass = 327
Molecular Formula = C22H21N3

Analytical Data

HPCL-MS (YMC ODS-A, 5 cm, $2\mu$, acetonitrile/water; API-ES): 2.75 min. 328.2 $C_{22}H_{21}N_3$=327.43

Biological Data

| Inhibition of bacterial growth: | | |
|---|---|---|
| Staph. aureus | c = 100 $\mu$M | 40% inhibition |
| Bac. subtilis | c = 100 $\mu$M | 76% inhibition |
| Strept. pneumoniae | c = 100 $\mu$M | 0% inhibition |
| Candida albicans | c = 100 $\mu$M | 0% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 0% inhibition |
| HepG2 | >100 $\mu$M | 0% inhibition |

EXAMPLE 8

3-(1—N-Isopropylethylamin-1H-imidazol-5-yl)-2-methyl-1H-indole

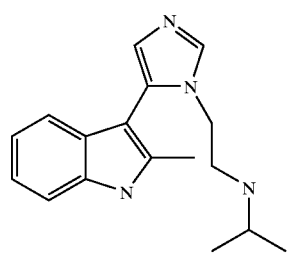

Molecular Weight = 282.39
Exact Mass = 282
Molecular Formula = C17H22N4

Analytical Data

HPLC-MS (YMC ODS-A, 5 cm, $2\mu$, acetonitrile/water; API-ES): 0.82 min. 283.2 $C_{17}H_{22}N_4$=282.39

Biological Data

| Inhibition of bacterial growth: | | |
|---|---|---|
| Staph. aureus | c = 100 $\mu$M | 82% inhibition |
| Bac. subtilis | c = 100 $\mu$M | 39% inhibition |
| Strept. pneumoniae | c = 100 $\mu$M | 0% inhibition |
| Candida albicans | c = 100 $\mu$M | 0% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 10% inhibition |
| HepG2 | >100 $\mu$M | 0% inhibition |

EXAMPLE 9

5-(Methoxy)-3-(1-(4-hydroxyphenyl)ethyl-1H-imidazol-5-yl)-1H-indole

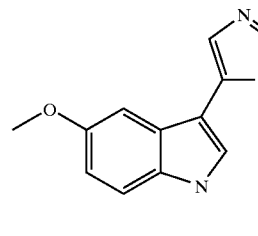

Molecular Weight = 333.39
Exact Mass = 333
Molecular Formula = C20H19N3O2

Analytical data

HPLC-MS (YMC ODS-A, 5 cm, $2\mu$, acetonitrile/water; API-ES): 2.26 min. 334.2 $C_{20}H_{19}N_3O_2$=333.39

Biological Data

| Inhibition of bacterial growth: | | |
|---|---|---|
| Staph. aureus | c = 100 $\mu$M | 25% inhibition |
| Bac. subtilis | c = 100 $\mu$M | 38% inhibition |
| Strept. pneumoniae | c = 100 $\mu$M | 85% inhibition |
| Candida albicans | c = 100 $\mu$M | 0% inhibition |
| Cytotoxicity L50: | | |
| A549 | >100 $\mu$M | |
| HepG2 | >100 $\mu$M | |
| Cell proliferation GI50: | | |
| A549 | >100 $\mu$M | 31% inhibition |
| HepG2 | >100 $\mu$M | 14% inhibition |

EXAMPLE 10

3-[5-(4-Fluoro-phenyl)-3-(1,2,3,4-tetrahydro-naphth-1-yl)-3H-imidazol-4-yl]-1H-indol

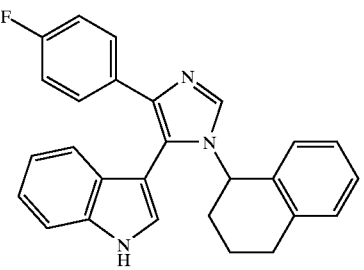

Molecular Weight = 407.49
Exact Mass = 407
Molecular Formula = C27H22FN3

Analytical Data
HPLC-MS (YMC ODS-A, 5 cm, 2µ, acetonitrile/water; API-ES): 3.425 min. [M+H]$^+$: 408.2 $^1$H-NMR (DMSO, 400 MHz): δ=1.531–1.666 (m, 1H); 1.838 (m, 1H); 2.009 (m, 2H); 2.691 (m, 1H); 2.810 (m, 1H); 5.011 (s, 1H); 6.811–7.703 (m, 14H); 11.574 (s, 1H, NH). $^{19}$F-NMR (DMSO, 376.81 MHz): δ–117.401 ppm

EXAMPLE 11

5-Benzyloxy-3-[5-(4-fluoro-phenyl)-3-(1,2,3,4-tetrahydro-naphth-1-yl)-3H-imidazol-4-yl]-1H-pyrrolo[2,3-c]pyridine

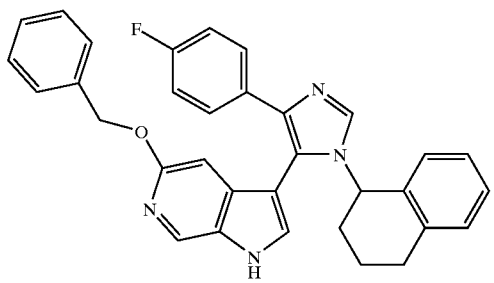

Molecular Weight = 514.61
Exact Mass = 514
Molecular Formula = C33H27FN4O

Analytical Data
HPLC-MS (YMC ODS-A, 5 cm, 2µ, acetonitrile/water; API-ES): 3.388 min. [M+H]$^+$: 515.2 $^1$H-NMR (DMSO, 400 MHz): δ=1.563–1.671(m, 1H), 1.880 (m, 2H), 1.934 (m, 1H); 2.665 (m, 1H), 2.775 (m, 1H); 4.996 (m, 1H); 5.352 (s, 2H); 6.486 (s, 1H); 6.834–7.547 (m, 15H); 8.435 (s, 1H); 9.896 (s, 1H); 11.790 (s, 1H, NH) $^{19}$F-NMR: (DMSO, 376.77 MHz): δ=–117.106 ppm
Biological Data

| Inhibition of bacterial growth: | | |
|---|---|---|
| Staph. aureus | c = 50 µM | 60% inhibition |
| Bac. subtilis | c = 50 µM | 80% inhibition |
| Candida albicans | c = 50 µM | 100% inhibition |

EXAMPLE 12

5-Benzyloxy-3-(3-indan-1-yl-3H-imidazol-4-yl)-1H-pyrrolo[2,3-c]pyridine

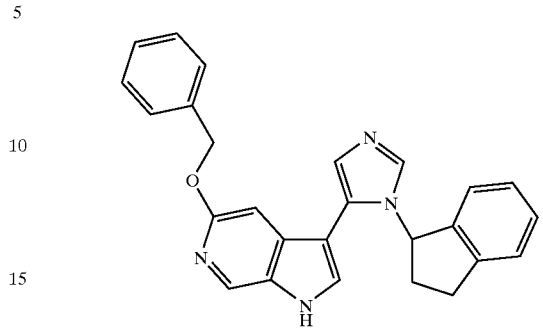

Molecular Weight = 406.49
Exact Mass = 406
Molecular Formula = C26H22N4O

Analytical Data
HPLC-MS (YMC ODS-A, 5 cm, 2µ, acetonitrile/water; API-ES): 2.987 min. [M+H]$^+$: 407.2 $^1$H-NMR (DMSO, 400 MHz): δ=1.880 (s, 1H); 2.178 (m, 1H); 2.827 (m, 1H); 2.971 (m, 1H); 5.315 (s, 2H); 5.647 (m, 1H); 6.826 (s, 1H); 6.967–7.435 (m,11H); 7.681 (s, 1H); 8.410 (s, 1H); 11.692 (s, 1H, NH)
Biological Data

| Inhibition of bacterial growth: | | |
|---|---|---|
| Staph. aureus | c = 12.5 µM | 80% inhibition |
| Bac. subtilis | c = 25 µM | 100% inhibition |
| Candida albicans | c = 100 µM | 60% inhibition |

EXAMPLE 13

1-[5-(5-Benzyloxy-1H-pyrrolo[2,3-c]pyrid-3-yl)-imidazol-1-yl]-indan-2-ol

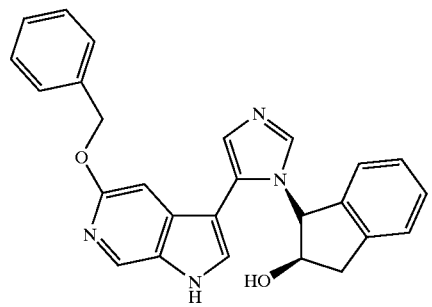

Molecular Weight = 422.49
Exact Mass = 422
Molecular Formula = C26H22N4O2

Analytical Data
HPLC-MS (YMC ODS-A, 5 cm, 2µ, acetonitrile/water; API-ES): 2.885 min. [M+H]$^+$: 423.2 $^1$H-NMR (DMSO, 400 MHz): δ=2.854–3.151(m, 3H); 4.121(m, 1H); 4.442(m, 1H); 5.303(s, 2H); 6.885(s, 1H); 7.013–7.400(m, 11H); 7.757(s, 1H); 8.415 (s, 1H); 11.688 (s, 1H, NH).

Biological Data

| Inhibition of bacterial growth: | | |
|---|---|---|
| Staph. aureus | c = 100 µM | 90% inhibition |
| Bac. subtilis | c = 100 µM | 90% inhibition |
| Candida albicans | c = 200 µM | 90% inhibition |

What is claimed is:
1. A compound of the formula (II)

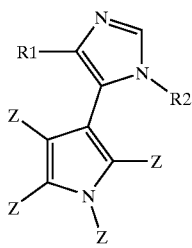

wherein
R1 is a hydrogen, an optionally substituted aryl or heteroaryl radical;
R2 is a halogen atom, pseudohalogen, an optionally substituted alkyl, alkenyl, aralkyl, aralkenyl, aralkynyl, cycloalkyl, cycloalkenyl, cycloalkynyl, cycloaralkyl, cycloaralkenyl, cycloaralkynyl, aryl or alkoxy radical or a non-aromatic or aromatic or partially aromatic heterocyclic ring;
At least two of the radicals Z taken together are part of an optionally substituted carbocyclic ring, to which one or two further, optionally substituted rings may be fused;
other occurrences of radicals Z in formula (II) denote, each independently of the others, a hydrogen atom, a halogen atom, a pseudohalogen, an optionally substituted alkyl, alkenyl, alkynyl, aralkyl, aralkenyl, aralkynyl, cycloalkyl, cycloalkenyl, cycloalkynyl, cycloaralkyl, cycloaralkenyl, cycloaralkynyl, aryl or alkoxy radical and/or an optionally substituted ring, to which one or two further, optionally substituted, rings may be fused.

2. A compound according to claim 1, which has the following formula:

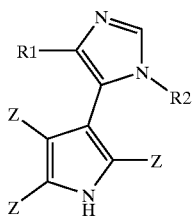

wherein
at least two of the radicals Z taken together are part of an optionally substituted carbocyclic ring, to which one or two further, optionally substituted rings may be fused;
the other occurrence of radical Z can denote, a hydrogen, a halogen, a pseudohalogen, an optionally substituted alkyl, alkenyl, alkynyl, aralkyl, aralkenyl, aralkynyl, cycloalkyl, cycloalkenyl, cycloalkynyl, cycloaralkyl, cycloaralkenyl, cycloaralkynyl, aryl or alkoxy radical or an optionally substituted ring, to which one or two further, optionally substituted rings may be fused.

3. A compound according to claim 2, wherein the radicals Z on adjacent carbon atoms of the pyrrole ring are part of an optionally substituted phenyl ring.

4. A compound according to one of the preceding claims, wherein R1 is an optionally substituted phenyl ring.

5. A compound according to any one of claims 1–3, wherein R2 is a cycloalkyl, to which an aryl or heteroaryl is fused.

6. Pharmaceutical composition comprising at least one 3-pyrroloimidazole derivative according to any one of claims 1–3, optionally in combination with carriers and/or adjuvants and/or excipients customary per se.

7. Pharmaceutical composition according to claim 6, which is formulated as a patch, ointment, paste, gel, cream, soluble powder, lotion, emulsion, spray, powder, suspension, suppository or injection solution.

8. Pharmaceutical composition according to claim 6, comprising at least one conjugate comprising a tumour-specific antibody and one or more compounds according to one of the preceding claims.

9. Pharmaceutical composition according to claim 6, wherein the active ingredients and, where applicable, the conjugates with tumour-specific antibodies are packed in liposomes.

10. A method of treatment or prevention of a tumour or cancer disease, the method comprising administering to a patient a 3-pyrroloimidazole derivative according to one of claims 1–3 or pharmaceutical composition thereof.

11. The method according to claim 10, characterized in that the tumour or cancer diseases are benign and malignant tumours that are solid or cystic in nature, adenomas, cystadenomas, papilloimas, adenocarcinonmas, adenocarcinonmas of the cirrhotic typo, basal cell carcinomas, sarcomas, fibrosarcomas, liposarcomas, lymphosarcomas, rhabdomyosarcomas, myxosarcomas, chondrosarcomas, reticulum cell sarcomas, Hodgkin's disease, embryonal tumours, neuroblastomas, nephtoblastomas, teratomas, adamantinomas, retroblastomas, haemangiomas, chordomas, odontomas, craniophacyngomas, hamartomas, lymphoangiomas, exostoses, neurofibrantosis, melanomas, lymphomas, hepatoblastomas, mammary carcinomas, cervical carcinomas, choriocarcinomas, adenoacanthomas, androblastomas, leiomyomas, arrhenoblastomas, Sertoli's cell tumours, theca and granulosa cell tumours, germinomas and seminomas, ovarian and vulvar carcinomas, urinary bladder and prostate carcinomas, tumours caused by schistosomiasis, astrocytomas, ependymogliomas, glioblastomas, medulloblastoma, oligodendrogliomas, spongioblastomas, meningeomas, tumours of Schwann's sheath cells, pinealomas, haemangioblastomas, osteoclastomas, Ewing's tumours, multiple myelomas, mycosis fungoides, Burkitt's tumours, leukaemias, acute and chronic lymphatic leukaemias, acute and chronic granulocytic leukaemias, acute and chronic monocytic leukaemias, stem cell leukaemias, basaliomas, fibromas, myomas, and metastases of any form of tumour that are accessible by surgical intervention in the form of a local injection.

12. A method for treatment or prevention of an infection by micro-organisms, the method comprising the administration of a 3-pyrroloimidazole derivative of any one of claims 1–3 or pharmaceutical composition thereof having antibiotic activity against micro-organisms.

13. A method of treatment or prevention according to claim 10, characterized in that the 3-pyrroloimidazole derivatives or pharmaceutical compositions are administered to the patient locally or systemically.

14. Pharmaceutical composition according to claim 7, comprising at least one conjugate comprising a tumour-specific antibody and one or more compounds according to one of the preceding claims.

15. Pharmaceutical composition according to claim 7, wherein the active ingredients and, where applicable, the conjugates with tumour-specific antibodies are packed in liposomes.

16. Pharmaceutical composition according to claim 8, wherein the active ingredients and, where applicable, the conjugates with tumor-specific antibodies are packed in liposomes.

17. Pharmaceutical composition according to claim 14, wherein the active ingredients and, where applicable, the conjugates with tumour-specific antibodies are packed in liposomes.

* * * * *